United States Patent [19]

Bruso

[11] Patent Number: 4,506,787

[45] Date of Patent: Mar. 26, 1985

[54] INSTRUMENT PROTECTOR

[75] Inventor: Loran H. Bruso, Ontario, Calif.

[73] Assignee: Warner-Lambert Company, Morris Plains, N.J.

[21] Appl. No.: 517,553

[22] Filed: Jul. 27, 1983

[51] Int. Cl.³ .................. B65D 73/00; B65D 85/00; B65D 65/24; A61B 17/06

[52] U.S. Cl. .................................. 206/363; 206/482

[58] Field of Search ............... 206/363, 482, 439, 370

[56] References Cited

U.S. PATENT DOCUMENTS

| | | | |
|---|---|---|---|
| 1,719,681 | 7/1929 | Wiebusch | 206/482 |
| 3,487,922 | 1/1970 | Peck | 206/80 |
| 3,604,616 | 9/1971 | Greif | 229/55 |
| 3,925,014 | 10/1975 | Langdon | 21/105 |
| 3,991,881 | 11/1976 | Augurt | 206/439 |
| 4,043,754 | 8/1977 | Sklar | 21/82 R |
| 4,142,632 | 3/1979 | Sandel | 206/363 |
| 4,385,692 | 5/1983 | Eldridge | 206/363 |

OTHER PUBLICATIONS

Trimedco Inc., Protect-O-Seal TM, Promotional Material 1983.

Primary Examiner—William T. Dixson, Jr.
Attorney, Agent, or Firm—Neil K. Nydegger

[57] ABSTRACT

A device for protecting medical instruments during sterilization and subsequent handling comprising a support member formed with a retaining loop for holding the instrument on the support member. A clear plastic sheet is joined at a portion of the margin of the support member to define a pocket into which the cutting edges of the medical instrument are placed for protection. For jointed instruments, the support member may also have an attached flap which is folded to position between the open handles of the instrument and thereby separate the instrument's cutting edges during the sterilization process.

5 Claims, 4 Drawing Figures

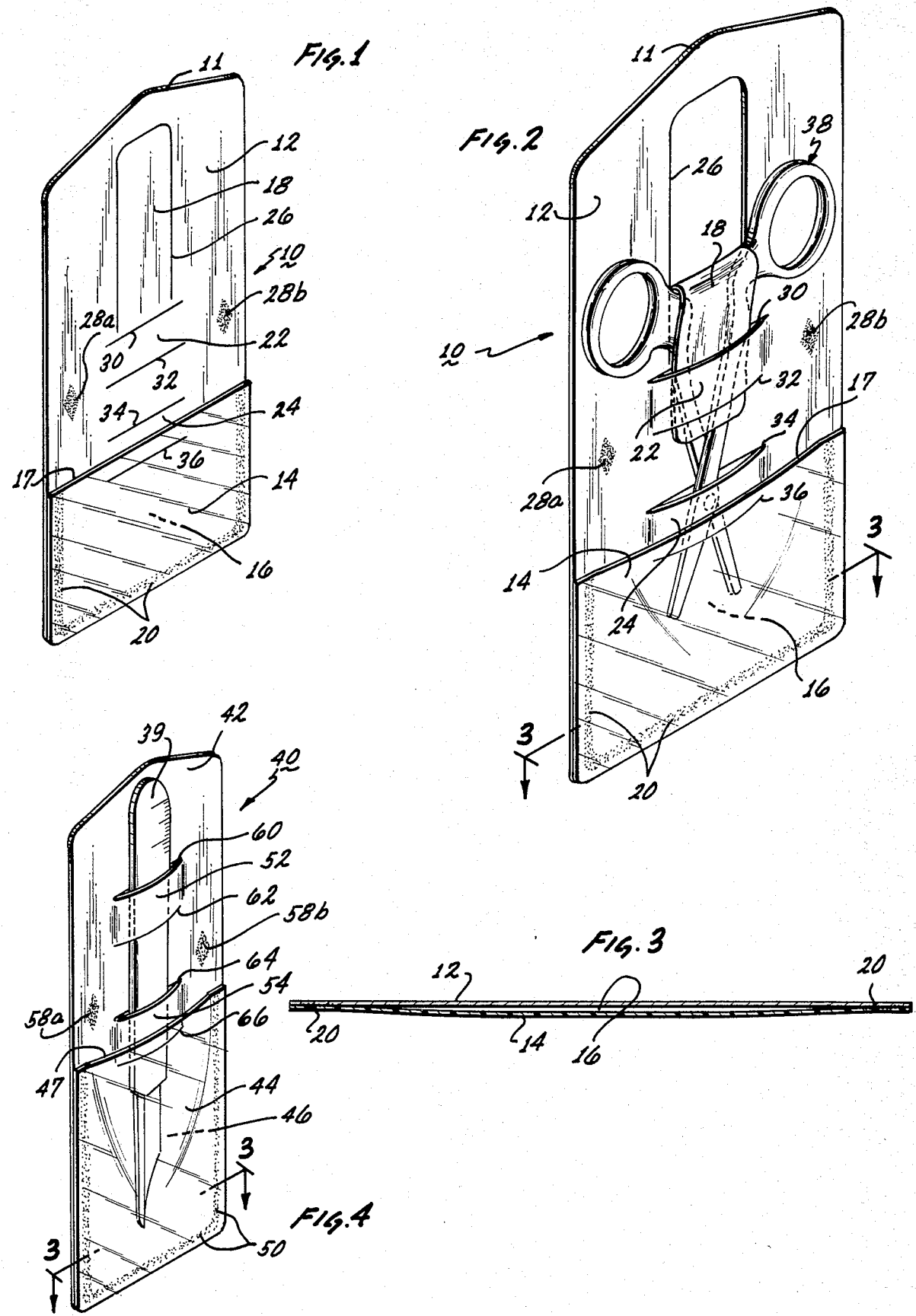

INSTRUMENT PROTECTOR

BACKGROUND OF THE INVENTION

This invention relates generally to packaging techniques and retaining devices for medical instruments. More particularly, this invention relates to a retaining device usable for protecting medical instruments during and after sterilization while providing for visual identification of the instrument.

DISCUSSION OF THE PRIOR ART

As is well known in the medical profession, the sterilization of precision medical instruments must be accomplished with certain purposes in mind. Basically, for both economic and efficiency reasons, such sterilization needs to be done in a manner which will ensure the most effective exposure of the instrument to the sterilizing medium as well as the minimum possibility of contaminating the instrument prior to its use. Obviously, a major concern in this process is the actual handling of the instrument. In order to meet the need for effective handling of a medical instrument during sterilization, various packaging techniques have been proposed. The prior art devices, however, do not incorporate into one package all of the features which are deemed desirable for the most effective handling of a medical instrument between the time it is sterilized and its subsequent use.

One desirable feature of an instrument protector is that it immobilize the instrument. Such immobilization, particularly for medical instruments which are pointed or which have cutting edges, reduces the possibility of dulling or blunting their surfaces by contact with or rubbing against other surfaces. Another desirable feature is that the instrument protector present the instrument for sterilization in a configuration which will allow the greatest exposure of the instrument to the sterilizing medium. For jointed instruments this means supporting them with the blades or extension members in a separated condition. Additionally, it is desirable if some provision is made for easy identification of the instrument. Preferably, such identification can be done visually and thus obviate the use of external labels which may cause confusion if the protector is used with a different instrument. This last consideration is particularly important when it is evisioned that one particular embodiment of a sterilizable instrument protector, such as is disclosed by the present invention, can be used with a plurality of different instruments. Finally, use of the instrument protector must be effective regardless of the particular sterilization process utilized.

Several containers and devices for holding medical instruments during sterilization processes are well known in the art. For example, U.S. Pat. No. 4,229,420 issued to Smith et al, U.S. Pat. No. 4,043,754 issued to Sklar and U.S. Pat. No. 3,925,014 issued to Langdon are directed to surgical instrument racks for holding medical instruments during sterilization. These inventions are, however, designed for the collective sterilization of complete sets of instruments and do not provide the versatility and flexibility achieved by sterilizing instruments in separate packages. Furthermore, when a plurality of instruments are simultaneously sterilized on the racks of these inventions, the retrieval of one instrument requires the exposure and possible contamination of all the others.

U.S. Pat. No. 4,385,692 issued to Eldridge entitled "Surgical Instrument Tip Protector and Method of Manufacture" discloses a protector for individual surgical instruments made of a sterilizable fine pore foam having a transparent window portion to permit identification of the instrument. This patent does not, however, teach or suggest the provision of means for retaining jaw-type jointed instruments, such as a scissors, in a blade separated position during the sterilization process. Further, the protector disclosed in this patent is made of a fine pore foam which, if snagged by the instrument, could cause particulate contamination. Also, it does not provide for a protector having a rigid support that facilitates its insertion into and immobilization within a sterilizable envelope of the type disclosed in U.S. Pat. No. 3,604,616 issued to Greif. Additionally, the instrument protector disclosed in this patent does not provide a suitable substratum on which chemical indicator inks can be imprinted.

For non-jointed instruments, such as scalpels and probes, the concerns are essentially the same as those discussed previously. With these instruments, however, the primary concern is to provide a stable support for the instrument which immobilizes the instrument on the support while permitting visual identification of the instrument. Whereas, U.S. Pat. No. 3,487,922 issued to Peck is directed to a cutlery display package having a transparent sheath, this patent does not suggest that its invention be used for sterilization of medical instruments. Moreover, it has certain distinguishable structural differences from the present invention. Specifically, the patent to Peck does not teach or suggest the use of die cut slits in the support to form a retaining strap for the instrument being protected.

Insofar as containers are concerned, U.S. Pat. No. 3,604,616 issued to Greif discloses a peel-open sterilizable envelope for retaining articles before, during and after sterilization. The patent also provides for an envelope which maintains sterility of the envelope's contents for extended periods of time. Although the invention of U.S. Pat. No. 3,604,616 allows for individual treatment of medical instruments, it does not teach or suggest means which would ease insertion of the instrument into the sterilizable envelope. Also, the patent does not teach a rigid support for immobilizing the medical instrument during the sterilization process.

Another desirable feature for an instrument protector is the ability to incorporate into the invention the use of chemical indicators that signify when the sterilization process has been completed. Typically, such indicators are specially formulated gas sensitive or steam sensitive inks of a type respectively disclosed in U.S. Pat. No. 3,098,751 issued to Huych et al and U.S. Pat. No. 2,118,144 issued to Berman et al. Such inks are particularly useful with the instrument protector of the present invention insofar as they signify when the instrument has been exposed to a particular sterilizing condition. Whereas, the present invention easily incorporates these inks, an instrument protector which is made with a foam, such as the device disclosed in U.S. Pat. No. 4,385,692 issued to Eldridge, would not provide the proper substratum for a chemical indicator ink.

Yet another desirable feature for an instrument protector is the added protection it can give against an inadvertent puncturing of the outer sterilizable envelope by the instrument's sharp or pointed surfaces. In the present invention, it is contemplated that the instrument's sharp and pointed surfaces will be sufficiently enclosed by appropriate materials to help guard against such an inadvertent puncturing.

In light of the above, it is an object of the present invention to provide an instrument protector having a rigid back for easy insertion into a peel pouch type sterilizable envelope. Additionally, the rigid back provides an appropriate substratum for chemical indicator inks. It is another object of the present invention to provide a means for holding jaw-type or jointed instruments in the blade separated position. Still another object of the present invention is to immobilize instruments within the sterilizable envelope during the sterilization process. A further object of the invention is to provide an inexpensive, easily manufactured instrument protector made of materials which have low particulate levels and which provide extra protection against a puncturing of the outer sterilizable envelope by the sharp or pointed surfaces of the instrument. Additionally, it is an object of the present invention to provide for a transparent pocket that allows easy identification of the medical instrument while it is held within the instrument protector.

SUMMARY OF THE INVENTION

A preferred embodiment of the novel instrument protector includes a support member having a retaining strap formed thereon for holding the instrument on the support member. A transparent film overlies a portion of the support member and is joined thereto at the margin of the support member to form a pocket into which the tip of the medical instrument is placed for protection. The support member is also formed with a flap. For jointed medical instruments, such as a scissors, the flap can be folded and retained in position between the handles of the instrument to thereby keep the blades in a separated condition during sterilization.

An alternate embodiment of the novel instrument protector is contemplated for use with a monadic instrument. In the alternate embodiment, the flap need not be used or it can be eliminated.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of an embodiment of the instrument protector;

FIG. 2 is a perspective view of the embodiment of FIG. 1 shown supporting a jointed medical instrument;

FIG. 3 is a cross sectional view of the instrument protector on line 3—3 of FIG. 2 and FIG. 4; and FIG. 4 is a perspective view of another embodiment of the instrument protector shown supporting a monadic instrument.

DESCRIPTION OF THE PREFERRED EMBODIMENTS

Referring to FIG. 1, there is shown, generally at 10, the instrument protector of the present invention. In the preferred embodiment of the instrument protector 10, the support member 12 is made from a semi-rigid material such as paper, cardboard, plastic or any other sheet stock which can withstand sterilization conditions. The support member 12 is generally rectangular in shape, but it may be formed with a taper 11 at one end of the support member 12 to facilitate insertion of the instrument protector into a sterilization envelope such as of the type disclosed in U.S. Pat. No. 3,604,616.

As can be seen in both FIG. 1 and FIG. 2, the support member 12 is constructed with die cut slits 30, 32, 34 and 36. Slits 30 and 32 are cut in order to form an upper retaining strap 22. Likewise, slits 34 and 36 are cut to form a lower retaining strap 24. The flap 18, shown in both FIG. 1 and FIG. 2, is formed by a die cut along the line 26. Also, support member 12 serves as a substratum for the chemical indicators 28a and 28b which are applied to the support member 12 by any means well known in the art. The preferred embodiments indicator 28a is a gas sensitive ink of the type disclosed in U.S. Pat. No. 3,098,751 and chemical indicator 28b is a steam sensitive ink of the type disclosed in U.S. Pat. No. 2,118,144.

A sheet 14 is attached at the margin of support member 12 along a line 20 by any means well known in the art, such as by heat sealing. This combination of the sheet 14 on support member 12 is for the purpose of forming a pocket 16. As can be best seen in FIG. 3, the pocket 16 is formed by the support member 12 and the sheet 14. In the preferred embodiments of the present invention, the lip 17 of the pocket 16, which is formed by the clear plastic material 14, is not joined with the support member 12. The lip 17 is positioned on the support member 12 to lie intermediate die cut slit 34 and die cut slit 36 which together form the lower retaining strap 24. This structure is provided to facilitate insertion of the blade portion of a medical instrument such as the scissors 38 into the pocket 16.

In its operation the instrument protector 10 is intended to rigidly retain a jointed medical instrument such as the scissors 38 shown in FIG. 2. In preparing the scissors 38 for sterilization with use of the instrument protector 10, the scissors 38 would be sequentially woven through slit 30, slit 32, slit 34 and slit 36 to be in position as shown in FIG. 2. As can be best seen in FIG. 2 after the medical instrument 38 has been woven through the slits 30, 32, 34 and 36 as described above, the tip end of the instrument lies within the pocket 16 defined by sheet 14 and support member 12. For jointed medical instruments such as scissors 38, the handles thereof can be spread to consequently spread the blades of the instrument. To retain the medical instrument in the blade separated condition, the flap 18 is folded between the handles of scissors 38 as shown in FIG. 2. Flap 18 is then sequentially inserted through the slit 30 and the slit 32 of the upper retaining strap 22. In this configuration, the instrument protector 10 rigidly holds a medical instrument, such as the scissors 38, and is ready for insertion into a sterilizable bag such as of the type disclosed in U.S. Pat. No. 3,604,616.

After sterilization, when the medical instrument is to be used, the instrument protector 10, with the medical instrument retained thereon, is removed from the envelope. Release of the tab 18 from the upper retaining strap 22 frees the medical instrument so it can be removed from the instrument protector and used for its intended purpose.

In an alternate preferred embodiment of the instrument protector shown in FIG. 4 and generally by the referenced character 40, it can be appreciated that there is no need for the flap 18 shown in FIG. 1 and FIG. 2. In all other respects the instrument protector 10 and the instrument protector 40 are substantially similar. The alternate preferred embodiment is, however, better suited when the medical instrument is not jointed and is, instead, a monadic instrument of the scalpel or probe type. More specifically, the alternate embodiment of an instrument protector 40 comprises a support member 42 which is of a semi-rigid material similar to the material described for instrument protector 10. In the instrument protector 40, the support member 42 is formed with the die cut slits 60, 62, 64 and 66. Respectively, slits 60 and 62 form an upper retaining strap 52 and the slits 64 and 66 form a lower retaining strap 54. Also, support member 42 has provision for incorporating chemical indicators 58a and 58b. The indicators 58a and 58b are substantially similar to the indicators 28a and 28b previously discussed and are preferably made from the same indicator inks.

Like instrument protector 10, the instrument protector 40 includes a clear plastic sheet 44 which is heat sealed to the support member 42 along the line 50. This joining of the sheet 44 to instrument protector 40 forms the pocket 46. A medical instrument, such as the scalpel 39 shown in FIG. 4, when prepared for sterilization, is sequentially woven through slits 60, 62, 64 and 66. Thus, positioned as shown in FIG. 4, the blade end of scalpel 39 is located within the pocket 46. As can be best appreciated by reference to FIG. 4, insertion of the medical instrument into pocket 46 is facilitated if the lip 47 of pocket 46 lies intermediate the slit 64 and 66 of the lower retaining strap 54.

A medical instrument, such as scalpel 39, in the configuration shown in FIG. 4, is prepared for sterilization and can be inserted into a sterilizable envelope such as of the type described in U.S. Pat. No. 3,604,616. When needed the sterilized instrument, together with the instrument protector 40, can be removed from the sterilizable envelope and used for its intended purposes.

While the particular instrument protector as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A sterilizable device for protecting a jointed medical instrument which comprises:
    a semi-rigid support member formed with an integral strap for holding the removable instrument on said support member;
    a flap formed by partial severance of said support member and being positioned for folding between the parted handles of said jointed instrument and under said integral strap to keep the handles and their associated tips in a separated condition; and
    a sheet overlying a portion of said support member and joined thereto at the margin of said support member to form an open-ended pocket thereover for protecting the instrument tips therein.

2. A device as cited in claim 1 wherein said support member is formed with a plurality of straps for removably holding the instrument on said support member.

3. A device as cited in claim 2 wherein said sheet is made of a transparent material.

4. A device as cited in claim 3 which further comprises a chemical indicator ink imprinted on said support member for indicating exposure of the medical instrument to a sterilization process.

5. A sterilizable device for protecting a jointed medical instrument which comprises:
    a semi-rigid support member formed with an integral strap holding the removable instrument on said support member;
    a flap formed by partial severance of said support member and being positioned by folding between the parted handles of said jointed instrument and under said integral strap keeping the handles and their associated tips in a separated condition; and
    a sheet overlying a portion of said support member and joined thereto at the margin of said support member forming an open-ended pocket thereover for protecting the instrument tips therein.

* * * * *